United States Patent [19]

Majoie

[11] 4,242,358
[45] Dec. 30, 1980

[54] METHOD OF TREATMENT OF ALGIAE
[75] Inventor: Bernard Majoie, Dijon, France
[73] Assignee: Societe de Recherches Industrielles (Sori), Paris, France
[21] Appl. No.: 6,105
[22] Filed: Jan. 24, 1979
[51] Int. Cl.³ .................... A61K 31/19; C07C 127/15
[52] U.S. Cl. ................................ 424/317; 260/501.11; 562/460
[58] Field of Search ...................... 424/317; 562/460
[56] References Cited
U.S. PATENT DOCUMENTS
3,995,056  11/1976  Allais et al. .......................... 424/317
FOREIGN PATENT DOCUMENTS
1268321  3/1972  United Kingdom ...................... 424/317
1415295  11/1975  United Kingdom ...................... 424/317

Primary Examiner—Dale R. Ore
Attorney, Agent, or Firm—Bacon & Thomas

[57] ABSTRACT

This invention is concerned with a new method of treatment of algiae which comprises administering to a patient in need of such a treatment a pharmaceutically effective amount of compound selected from the group consisting of (i) m-benzoyl-phenoxyalkylcarboxylic acids of the formula

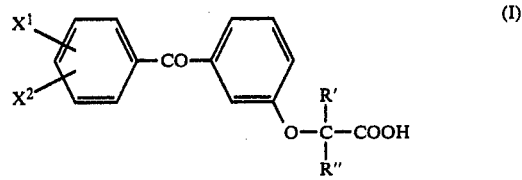

Wherein $X^1$ and $X^2$ are the same or different and are each hydrogen, methyl, methoxy, chlorine, fluorine, bromine or trifluoromethyl, and R' and R" are the same or different and are each hydrogen or methyl; and (ii) non-toxic metallic salts thereof.

15 Claims, No Drawings

METHOD OF TREATMENT OF ALGIAE

OBJECT OF THE INVENTION

This invention relates to a new method of treatment of algiae which comprises administering to a patient needing such a treatment a pharmaceutically effective amount of a compound selected from the group consisting of
(i) m-benzoyl-phenoxyalkylcarboxylic acids of the formula

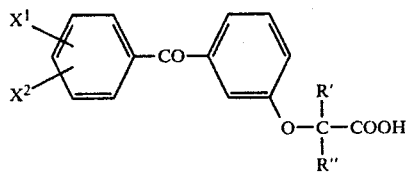

in which $X^1$ and $X^2$ are the same or different and are each H, $CH_3$, $OCH_3$, F, Cl, Br or $CF_3$, and R' and R" are the same or different and are each H or $CH_3$; and
(ii) non-toxic metallic salts thereof.

This invention is also concerned with some compounds of the general formula I which are novel and claimed as compounds per se.

RELEVANT PRIOR ART

It is known that p-benzoyl-phenoxyalkylcarboxylic acids, their ester derivatives and amide derivatives have already been proposed as lipid and cholesterol reducing agents, in particular in British Pat. Nos. 1,268,321 and 1,415,295. One of these compounds, namely isopropyl 2-[4-(chlorobenzoyl)-phenoxy]-2-methyl-propionate, is now commercialized as hypocholesterolaemiant and hypolipidaemiant under the name of LIPANTHYL, and has been the subject of several pharmacological publications, in particular by SORNAY et al., Arzneimittel-Forschung Drug Research (1976) pages 885–889; GURRIERI et al; ibidem, pages 889–894; LUU-DUC et al, ibidem, pages 894–895; BRODIE et al, ibidem, pages 896–901; ROUFFY et al, ibidem, pages 901–906; and WULFERT et al, ibidem, pages 906–909.

In my previous U.S. patent application Ser. No. 714,504 filed on Aug. 16, 1976, now U.S. Pat. No. 4,146,385 m-benzoyl-phenoxyalkylcarboxylic acids their ester derivatives and amide derivatives have been disclosed as lipid and cholesterol reducing agents.

I have now found that the m-benzoyl-phenoxyalkylcarboxylic acids according to formula I and their non-toxic metallic salts are useful as antalgic agents.

DETAILED DESCRIPTION OF THE INVENTION

The acids of formula I are prepared according to a method known per se. For instance one of the two routes (a) and (b) disclosed in my above mentioned U.S. patent application can be used. The metallic salts are prepared by a method known per se, using classical reactions.

The preferred compounds useful as antalgic according to the invention are those in which the $X^1X^2C_6H_3$ radical represents a phenyl, 4-methoxyphenyl, 3-trifluoromethylphenyl, 2,4-dichlorophenyl, 2-tolyl, 3-tolyl, 4-tolyl, 2,4-dimethylphenyl or 3,4-dimethylphenyl group.

The preferred salts are the sodium ones which are very soluble in water (their solubility in water being higher than or equal to 50 g/l).

The best mode for carrying out the method of treatment of the invention consists in administering to human beings the acids of formula I per oral route, and the sodium salts by injectable route in aqueous solution.

The most interesting compound of formula I as antalgic agent is the 2-(3-benzoyl)-phenoxy-2-methylpropionic acid (see example 1) which is coded as compound 599.

Table I, below, shows illustrative compounds of formula I. Examples 1–5 have been disclosed in my previous U.S. patent application Ser. No. 714,504. Examples 6–13 are novel compounds, which present interesting pharmaceutical properties namely (i) an antalgic activity, and (ii), besides said antalgic activity but at a lower level, a hypolipemic and hypocholesterolemic activity, and an anti-inflammatory activity.

The antalgic activity of the compounds of formula I was determined by measuring the cramping induced by phenylbenzoquinone, as described by Siegmund et al, Proc. Soc. Exp. Biol. Med. (1975) 95, 729. A painful reaction, characterized by twisting movements and elongation of the abdomen, with scraping of the rear paws, was introduced by the intraperitoneal administration of a 0.02% w/v solution of phenyl-benzoquinone in 95% alcohol at a rate of 0.5 ml/20 g body weight. The activity was measured by the percentage inhibition in the number of painful symptons over 5 minutes. The results are summarized in table II, below, wherein each compound to be tested was administered to mice per i.p. route (at a dose corresponding to the tenth of its LD-50 mice i.p.), and simultaneously checked in parallel with an antalgic substance of reference, namely Glaphenine i.e. 2,3-dihdroxypropyl N-(7-chloro-4-quinolyl)-anthranilate. The LD-50 values (on mice by i.p. route) of Examples 1–13 are also given in table II.

The data of table II show that the compounds according to this invention are at least as active as, and in general, more active than Glaphenine as antalgic agents. Moreover they are well tolerated and do not induce the kidney troubles of Glaphenine.

TABLE I

| Example | Code No. | $X^1$ | $X^2$ | R' | R" | Melting point |
|---|---|---|---|---|---|---|
| 1 | 599 | H | H | $CH_3$ | $CH_3$ | 90° C. |
| 2 | 600 | 4-$OCH_3$ | H | $CH_3$ | $CH_3$ | 98° C. |
| 3 | 650 | 3-$CF_3$ | H | $CH_3$ | $CH_3$ | 80° C. |
| 4 | 671 | 4-$CH_3$ | H | $CH_3$ | $CH_3$ | 98° C. |
| 5 | 712 | 3-$CH_3$ | 4-$CH_3$ | $CH_3$ | $CH_3$ | 94° C. |
| 6 | 767 | H | H | H | $CH_3$ | 118° C. |
| 7 | 785 | 3-$CF_3$ | H | H | $CH_3$ | 100° C. |
| 8 | 797 | 2-Cl | 4-Cl | H | $CH_3$ | 170° C. |
| 9 | 798 | 2-Cl | 4-Cl | H | H | 112° C. |
| 10 | 1232 | 2-$CH_3$ | 4-$CH_3$ | $CH_3$ | $CH_3$ | ≦45° C. |
| 11 | 1236 | 2-$CH_3$ | H | $CH_3$ | $CH_3$ | 78° C. |
| 12 | 1247 | 4-$CH_3$ | H | H | H | 115° C. |
| 13 | 1248 | 4-$CH_3$ | H | H | $CH_3$ | 118° C. |

TABLE II

| Example | Code No. | LD-50 mice i.p. (mg/kg) | Percentage of diminution of cramping | |
|---|---|---|---|---|
| | | | Glaphenine | Tested compound |
| 1[a] | 559 | 350 | 67 | 95 |
| 2 | 600 | 300 | 97 | 97 |
| 3 | 650 | 300 | 54 | 43 |
| 4 | 671 | 400 | 54 | 66 |
| 5 | 712 | 450 | 92 | 100 |
| 6 | 767 | 770 | 54 | 100 |
| 7 | 785 | 350 | 52 | 61 |
| 8 | 797 | 800 | 94 | 100 |
| 9 | 798 | 350 | 62 | 94 |
| 10 | 1232 | 600 | 69 | 69 |
| 11 | 1236 | 600 | 71 | 70 |
| 12 | 1247 | 450 | 55 | 92 |
| 13 | 1248 | 700 | 55 | 98 |

Note:
[a]Example 1 exhibits a LD-50 mice per os of 350 mg/kg, a LD-0 rat per os higher than 1600 mg/kg, a KD-0 rat i.p. of 540 mg/kg; and a ED-50 mice per os antalgic activity of 35 mg/kg (without kidney troubles) while Glaphenine exhibits a ED-50 mice per os antalgic activity of 25 mg/kg and induces kidney troubles.

This invention provides pharmaceutical compositions comprising a compound or salt of the invention in association with a physiologically acceptable excipient.

The compounds of this invention in particular the acids may be administered orally to man, for example in the form of capsules or tablets (sweetened or unsweetened) or in an injectable form. For the purposes of preparing capsules, the active substance may be mixed with, for example, magnesium stearate, amigel and an excipient such as lactose. After filling, capsules containing, say, 200 mg of the active substance may be prepared. In preparing tablets, the active substance may be mixed with lactose and icing sugar. The mixture may be granulated in a fluidised bed and the granules which are obtained may be tabletted in the presence of magnesium stearate.

In preparing injectable compositions, a soluble form of one of the active compounds, in particular the sodium salt, may be dissolved in water at a concentration of about 50-250 g/l, subjected to sterile filtration and lyophilised under the same sterile conditions. The lyophilisate may then be bottled with physiological serum.

The compound of Example 1 has been tested clinically as an antalgic agent on 41 patients. A double blind test was carried out, using placebos and a dose of 400 mg per day of the active compound, administered as tablets. The test was carried out over 20 days; the tolerance of the product as proved to be excellent and its activity good in 80% of cases, where the patients had received the active compound, and the symptoms had been relieved.

What is claimed is:

1. A method of treatment of algiae which comprises administering to a patient in need of such a treatment an effective antalgic amount of a compound selected from the group consisting of
(i) m-benzoyl-phenoxyalkylcarboxylic acids of the formula

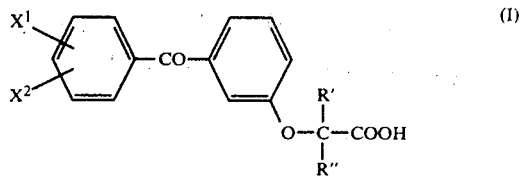

wherein $X^1$ and $X^2$ are the same or different and are each H, $CH_3$, $OCH_3$, F, Cl, Br or $CF_3$, and R' and R" are the same or different and are each H or $CH_3$; and,
(ii) non-toxic metallic salts thereof.

2. A method of treatment according to claim 1 in which the metallic salt is a sodium salt.

3. A method of treatment according to claim 1 in which the antalgic compound is the 2-[(3-benzoyl)-phenoxy] 2-methylpropionic acid or its sodium salt.

4. A method of treatment according to claim 1 in which the antalgic compound is the 2-[3-(4-methoxybenzoyl)-phenoxy]-2-methylpropionic acid or its sodium salt.

5. A method of treatment according to claim 1 in which the antalgic compound is the 2-[3-(3-trifluoromethylbenzoyl)-phenoxy]-2-methylpropionic acid or its sodium salt.

6. A method of treatment according to claim 1 in which the antalgic compound is the 2-[3-(4-methylbenzoyl)-phenoxy]-2-methylpropionic acid or its sodium salt.

7. A method of treatment according to claim 1 in which the antalgic compound is the 2-[3-(3,4-dimethylbenzoyl)-phenoxy]-2-methylpropionic acid or its sodium salt.

8. A method of treatment according to claim 1 in which the antalgic compound is the 2-[(3-benzoyl)-phenoxy]-propionic acid or its sodium salt.

9. A method of treatment according to claim 1 in which the antalgic compound is the 2-[3-(3-trifluoromethylbenzoyl)-phenoxy]-propionic acid or its sodium salt.

10. A method of treatment according to claim 1 in which the antalgic compound is the 2-[3-(2,4-dichlorobenzoyl)-phenoxy]-propionic acid or its sodium salt.

11. A method of treatment according to claim 1 in which the antalgic compound is the 3-(2,4-dichlorobenzoyl)-phenoxyacetic acid or its sodium salt.

12. A method of treatment according to claim 1 in which the antalgic compound is the 2-[3-(2,4-dimethylbenzoyl)-phenoxy]-2-methylpropionic acid or its sodium salt.

13. A method of treatment according to claim 1 in which the antalgic compound is the 2-[3-(2-methylbenzoyl)-phenoxy]-2-methylpropionic acid or its sodium salt.

14. A method of treatment according to claim 1 in which the antalgic compound is the 3-(4-methylbenzoyl)-phenoxyacetic acid or its sodium salt.

15. A method of treatment according to claim 1 in which the antalgic compound is the 2-[3-(4-methylbenzoyl)-phenoxy]-propionic acid or its sodium salt.

* * * * *